US005552135A

United States Patent [19]

Cioca et al.

[11] Patent Number: 5,552,135

[45] Date of Patent: Sep. 3, 1996

[54] SUNSCREENS CONTAINING PLANT EXTRACTS

[75] Inventors: Gheorghe Cioca, Lake Grove; Jon E. Anderson, Bayside; Isaac D. Cohen, Brooklyn; Charles C. Tadlock, Islip Terrace; Andrew J. Bevacqua, East Setauket, all of N.Y.

[73] Assignee: Estee Lauder, Inc., Melville, N.Y.

[21] Appl. No.: 22,238

[22] Filed: Feb. 25, 1993

[51] Int. Cl.⁶ .................................................. A61K 7/42
[52] U.S. Cl. .................................. 424/59; 424/60
[58] Field of Search .............................. 424/195.1, 59

[56] References Cited

U.S. PATENT DOCUMENTS

| | | | |
|---|---|---|---|
| 3,988,436 | 10/1976 | Loo | 424/59 |
| 4,014,995 | 3/1977 | Juliano et al. | 424/168 |
| 4,844,890 | 7/1989 | Suskin | 424/73 |
| 4,943,433 | 7/1990 | Rudov | 424/195.1 |
| 5,079,005 | 1/1992 | Gupta | 424/408 |
| 5,204,105 | 4/1993 | Mausner | 424/401 |

FOREIGN PATENT DOCUMENTS

| | | |
|---|---|---|
| 1022851 | 12/1977 | Canada. |
| 2115229 | 2/1994 | Canada. |
| 2115228 | 2/1994 | Canada. |
| 0201956 | 4/1986 | European Pat. Off.. |
| 0275719A2 | 7/1988 | European Pat. Off.. |
| 0471584 | 8/1991 | European Pat. Off.. |
| 2243676 | 9/1974 | France. |
| 2692783 | 6/1992 | France. |
| 62-249918 | 10/1987 | Japan. |
| 63-284117 | 11/1988 | Japan. |
| WO9115117 | 10/1991 | WIPO. |

OTHER PUBLICATIONS

Chemical Abstracts, vol. 113 (18):158451j, 1990 (Abst. of DE-89-3938284).
Chemical Abstracts (I), vol. 94 (6):36122w, 1980, (Abst. of CA 1085302).
Chemical Abstracts (II), vol. 86 (18):127106v, 1976, (Abst. of Neth7505930).
Derwent Abstract (I), C85-070375, May 1985, (Abst. of FR2555, 447).
Derwent Abstract (II) 74-37970V [17], Aug. 1993, (Abst. of JP49013972 B).
Derwent Abstract, 1990 (III), (De3938284 abstract) Nov. 1989.
Derwent Abstracts, Sep. 1989, (Abst. of JP01502820W).
Database WPI, Week 7321, Derwent Publications Ltd., London G.B.-AN 73-30029U (Abstract of JP-A-48015 616 (Hagihara)).
A. S. Chawla et al., "Anti-Inflammatory Action of Ferulic Acid and its Esters in Carrageenan Induced Rat Paw Oedema Model", Indian Journal of Experimental Biology, 25:187–189 (1987).
D. G. H. Daniels et al., "Antioxidants in Oats: Mono–Esters of Caffeic and Ferulic Acids", J. Sci. Fd Agric., 18:589–595 (1967).
Ibata, Y., "Natural Sunscreen Agents—Useful Plant of Animal Extracts for Sun Care Products", Fragrance Journal, 15 (3), 54 (1987).

Primary Examiner—Alan L. Rotman
Attorney, Agent, or Firm—Pennie & Edmonds

[57] ABSTRACT

Improved sunscreen compositions and their methods of manufacture are provided. The sunscreen compositions include extracts of cereal plants and an optional sunscreen blocking agent. The compositions optionally also may include dihydroxycinnamic derivatives.

21 Claims, No Drawings

SUNSCREENS CONTAINING PLANT EXTRACTS

FIELD OF THE INVENTION

The invention relates to sunscreen compositions. More particularly, the invention relates to sunscreen compositions that employ extracts of cereal plants such as oats.

BACKGROUND OF THE INVENTION

Excessive exposure of human skin to either the rays of the sun or to sun lamps which emit ultraviolet radiation similar to natural sunlight can result in sunburn or erythema solars as the condition is medically defined.

In order to substantially reduce or prevent sunburn, various sunscreen compositions have been proposed which contain sunscreen agents which scatter the sunlight, or which absorb the ultraviolet portion of the sun's radiant energy, i.e., energy radiation equivalent to about 2800 to about 4000 angstrom units.

For topical application, sunscreen compositions must be non-toxic and non-irritating to the skin, and capable of application to the skin as a uniform continuous film. In addition, the active sunscreening agents in the sunscreen compositions must be chemically stable. In particular, the sunscreening agents must be resistant to chemical and photodegradation when on the skin, as well as resistant to absorption through the skin.

A wide variety of sunscreen preparations are available. Sunscreens which have both functional and aesthetic characteristics, however, are nevertheless sought. Typically, the sunscreen preparations of the art have been chemically-based compositions that employ synthetic materials such as para-aminobenzoic acid (PABA) derivatives as the sunscreen agent. Although the chemically-based sunscreen compositions of the art have been effective in reducing sunburn, many users suffer allergic reactions to these products. Also, uncertainty exists over the effects of long term exposure of the skin to chemically-based sunscreen compositions.

A need therefore exists for sunscreen formulations that employ a minimum of synthetic chemical ingredients but yet provide effective protection against ultraviolet light absorption.

SUMMARY OF THE INVENTION

Improved sunscreen compositions and their methods of manufacture are provided. The sunscreen compositions include extracts of cereal plants, and a vehicle for enabling the mixture to be applied to skin. The sunscreen compositions can further include sunscreen blocking agents such as $TiO_2$. The compositions further may include dihydroxycinnamic acid derivatives such as ferulic acid and ethyl ferulate.

The present invention involves the discovery that extracts of cereal plants such as oat plants advantageously can be incorporated into sunscreen formulations to provide sunscreen compositions. In accordance with the invention, aqueous extracts of cereal plants, or hydroalcoholic extracts of cereal plants, such as aqueous ethanol cereal extracts, aqueous methanol cereal extracts, and the like, are employed with a vehicle to provide sunscreen compositions. These compositions further can be combined with well known sunscreen agents such as $TiO_2$ to provide compositions with an SPF that is surprisingly larger than the SPF provided by compositions which employ only a sunscreen agent. Useful extracts may be obtained from cereal plants such as oats, corn, wheat, barley, rye, rice, and mixtures thereof. Useful vehicles may include any of water, water-based liquids, oils, gels, emulsions, dispersions, or mixtures thereof, especially water. The sunscreen compositions may be employed in a variety of cosmetic formulations such as creams, gels, powders, lotions, and the like.

DETAILED DESCRIPTION OF THE INVENTION

The sunscreen compositions of the invention are produced by combining extracts of cereal plants and a vehicle for enabling the sunscreen composition to be applied to the skin. Useful cereal plant extracts such as those of oats, corn, wheat, barley, rye, rice, and mixtures thereof, especially those containing oats, may be employed. These cereal plant extracts may include, but are not limited to, water-soluble extracts such as those of water, water-alcohol mixtures, glycols, water-glycol mixtures and the like, hydroalcoholic extracts such as water-ethanol extracts and the like, most especially oat water-ethanol extracts; oil extracts such as those of mineral oil, silicones, and the like; alcohol-soluble extracts such as those of ethanol, methanol, propanol, and the like, especially ethanol. Sunscreen agents which may be employed in the invention include but are not limited to well known sunscreen agents such as aminobenzoic acid, cinoxate, diethanolamine p-methoxycinnamate, digalloyl trioleate, dioxybenzone, ethyl 4-[bis(hydroxypropyl)] aminobenzoate, 2-ethylhexyl 2-cyano-3,3-diphenylacrylate, 2-ethylhexyl p-methoxycinnamate, 2-ethylhexyl salicylate, glyceryl aminobenzoate, homosalate, lawsone with dihydroxyacetone, menthyl anthranilate, oxybenzone, padimate A, padimate O, 2-phenylbenzimidazole-5-sulfonic acid, red petrolatum, sulisobenzone, titanium dioxide, triethanolamine salicylate, preferably titanium dioxide.

Cereal plant extracts for use in the invention generally can be made by treating portions of cereal plants such as oats with extraction agents by methods known in the art to provide corresponding extracts thereof. See F. M. Webster, *Oats: Chemistry and Technology*, 1986. Useful extraction agents generally may include water, mineral oil, hydrocarbons, silicones, fatty acids, fatty acid derivatives, waxes, and mixtures thereof, especially water and an aliphatic alcohol, most preferably water and ethanol. Hydrophobic extraction agents as well as hydrophilic extraction agents also may be employed. Useful hydrophobic extraction agents may include fatty acids such as myristic acid and the like; esters such as isopropyl myristate and the like; diesters such as diisopropyl adipate and the like; triesters such as caprylic/capric triglyceride and the like; hydrocarbons such as isododecane, petrolatum and the like; waxes such as beeswax and the like; silicones such as cyclomethicone, dimethicone, and derivatives thereof such as dimethicone copolyol.

Hydrophilic extraction agents which may be employed include water, lower molecular weight aliphatic alcohols such as ethanol, methanol, propanol and the like; diols such as propylene glycol, butylene glycol and the like; polyols such as glycerine and the like; polyol-derived materials such as polyoxyethylene (7) glyceryl triacetate; and polymers of ethylene oxide such as polyethylene glycol 200.

Useful extraction agents also may include volatile liquids. Such liquids are in the liquid state at room temperature (above 22° C.) and evaporate completely from the skin within thirty minutes after application. Volatile liquid vehicles that may be employed as extraction agents include but are not limited to trichlorofluoromethane, isopropanol and $C_{10}$-$C_{16}$ isoparaffins, $C_{12}$-$C_{14}$ isoparaffins, and volatile silicones. The amount of volatile liquid vehicles readily may be determined by the art skilled. Other extraction agents will be apparent to those skilled in the art.

Preferably in the present invention, the plant extract is derived by washing plant material in the form of ground or groats of cereal plants in a solution of chloroform and methanol. The plant material is separated from the solution, dried, and treated with a 1:1 mixture of water and ethanol to provide a water-ethanol composition containing the plant extract and undissolved plant material. The water-ethanol composition containing the extract then is separated from the plant material. The resulting mixture is concentrated, preferably under reduced pressure, and taken to dryness to provide a residue. The residue is washed with absolute ethanol or 99% ethanol, and filtered to provide the plant extract. The plant extract then is dried. The foregoing procedure may be applied to a variety of cereal plants such as oats, corn, wheat, barley, rye, rice, and mixtures thereof to yield extracts. Water extracts of oats, water-ethanol extracts of oats, and ethanol extracts of oats, however, are preferred.

The extract of the cereal plant may be used in the sunscreens of the invention in the form in which it initially is derived. Alternatively, the extract may be concentrated to remove a portion or substantially all of its liquid content. For example, the extract may be concentrated under reduced pressure via well known equipment such as a rotary evaporator, flash evaporator, rising film evaporator, thin film evaporator, or contherm evaporator to provide a liquid concentrate which can be blended with a vehicle. Alternatively, the concentrate thoroughly can be dried using well known equipment such as a rotary evaporator, spray dryer, or freeze dryer to yield a powder which can be blended with a vehicle.

The vehicle employed in the sunscreen compositions may be any suitable material such as gases, water, water-based solutions, lotion, dispersion, emulsion, oil, oil-based solutions, gel or powder. The amount of vehicle in the sunscreen composition readily can be determined by those skilled in the art, depending on composition.

Gels useful as vehicles for the sunscreen compositions of the invention conveniently can be produced by mixing an oil with an organoclay. The resulting gel may be combined with a desired amount of the sunscreen agents and cereal plant extracts according to the SPF desired. The specific amount of sunscreen agent and cereal plant extract for providing a desired SPF readily can be determined by those skilled in the art.

Hydrophobic vehicles as well as hydrophilic vehicles may be employed in the sunscreen compositions of the invention. Useful hydrophobic vehicles may include fatty acids such as myristic acid, stearic acid and the like; fatty alcohols such as cetyl alcohol, stearyl alcohol and the like; esters such as isopropyl myristate; diesters such as diisopropyl adipate; triesters such as caprylic/capric triglycerides; hydrocarbons such as isododecane and petrolatum; waxes such as beeswax; silicones such as cyclomethicone and dimethicone, and derivatives thereof such as dimethicone copolyol, and mixtures thereof.

Hydrophilic vehicles which may be used in the sunscreen compositions of the invention include water, lower molecular weight aliphatic alcohols such as ethanol, methanol and propanol; diols such as propylene glycol and butylene glycol; polyols such as glycerine; polyol-derived materials such as polyoxyethylene(7) glyceryl triacetate; and polymers of ethylene oxide such as polyethylene glycol 200, and mixtures thereof.

Useful vehicles also may include volatile liquids. Such liquids are in the liquid state at room temperature (about 22° C.) and evaporate completely from the skin within thirty minutes after application. Volatile liquid vehicles that may be employed include but are not limited to trichlorofluoromethane, isopropanol and $C_{10}$-$C_{16}$ isoparaffins, $C_{12}$-$C_{14}$ isoparaffins, and volatile silicones. The amount of volatile liquid vehicles readily may be determined by the art skilled.

The sunscreen compositions further may include a preservation agent such as an anti-microbial agent to inhibit growth, reproduction or activity of contaminating organisms that may be present in the composition. Other additives which may be combined with the sunscreen compositions include moisturizers, humectants, emollients, emulsifiers, thickeners, stabilizers, fragrances, colorants, skin treatment materials such as vitamin E, and the like.

As indicated, the sunscreen compositions of the invention are made by formulating a composition incorporating cereal plant extracts, optionally one or more sunscreen agents, and a vehicle. Preferably, oat extracts, most preferably aqueous oat extracts, ethanol oat extracts, and aqueous oat ethanol extracts, are employed. The oat extracts may be used in sunscreen formulations in amounts of from 0.1 to 50% by weight, preferably 0.5 to 15%, more preferably 0.5 to 5%, most preferably 2%. The specific amounts of sunscreen agent employed with the extract to achieve a desired SPF readily can be determined by those skilled in the art.

Dihydroxycinnamic acid derivatives such as ferulic acid and ferulic acid esters, particularly ethyl ferulate, may be included in the sunscreen compositions of the invention. The dihydroxycinnamic acid derivatives may be present in amounts of 0.05–25% by weight, preferably 0.5 to 10%, most preferably 0.5 to 5%. Ferulic acid and ethyl ferulate may be purchased from Aldrich Chemical Co., and ICN Biomedicals, Inc., Cleveland, Ohio.

The sunscreen compositions conveniently may be provided in a variety of forms, such as liquids, creams, and sprays. Useful sprays may include any conventional hydrocarbon propellant. The propellant typically may be present in an amount within the range of 5 to 15% by weight of the total composition. Hydrocarbon propellants may include a mixture of isobutane and propane. Other mixtures of hydrocarbon propellants which may be employed include butane, propane, and dimethyl ether.

The sunscreen compositions of the invention also may be combined with cosmetic preparations, such as skin lotions, cold creams, lipsticks, and the like which when applied to the skin are directly exposed to ultraviolet ("UV") light. Methods of formulating cosmetic preparations are known. The sunscreens of the invention, when combined with moisturizing creams, lotions and the like, therefore, may be used to provide protection from UV light absorption as well as to impart a soft, smooth residual feel to the skin.

The SPF of the sunscreen formulations of the invention is evaluated by the in vivo method as described in the *Federal Register*, 43(166), pp38206–38269, Friday, Aug. 25, 1978, Part II (full title: Dept. of Health, Education, and Welfare, Food and Drug Admin. —"Sunscreen Products for Over-The-Counter Human Drugs, Proposed Safety, Effective and Labeling Conditions").

EXAMPLE 1

Master Batch (1) is formulated by combining the components thereof at room temperature with a Silverson-type homogenizing mixer. Master Batch (1) then is heated to 80° C. while mixing with a Lightnin™ propeller mixer. Master Batch (2) likewise is formed by combining the ingredients thereof at 78° C. and mixing with a Lightnin™ propeller mixer. Master batches (1) and (2) then are combined and mixed with a Silverson-type homogenizing mixer, mixed for 5 minutes, and cooled to 32° C. to provide a first blend. Master batch (3) is formed by mixing the components thereof with a Lightnin™ propeller mixer at room temperature, and the resulting mixture is added to the first blend to provide a second blend that is cooled to 30° C. Master batch (4), formed by mixing the components thereof in a Lightnin™ propeller mixer at room temperature, then is added to the second blend. The compositions of master batches (1)–(4) are given in Tables 1–4, respectively.

TABLE 1

| COMPONENT | PERCENT |
| --- | --- |
| Hetester PHA[1] | 10.00 |
| Finsolv TN[2] | 10.00 |
| SAT-UFTR TiO$_2$[3] | 7.00 |

[1]From Bernel Chemical Co.
[2]From FineTex Chemical
[3]From U.S. Cosmetics Co.

TABLE 2

| COMPONENT | PERCENT |
| --- | --- |
| Deionized water | 59.65 |
| Veegum R[4] | 0.70 |
| Keltrol F[5] | 0.30 |
| Methylparaben[6] | 0.15 |

[4]From R. T. Vanderbilt Co.
[5]From Kelco Chemical Co.
[6]From Nipa Chemical Co., Japan

TABLE 3

| COMPONENT | PERCENT |
| --- | --- |
| Deionized water | 2.00 |
| Germall 115[7] | 0.20 |

[7]From Sutton Laboratories

TABLE 4

| COMPONENT | PERCENT |
| --- | --- |
| Deionized Water | 8.00 |
| Water-ethanol Oat Extract | 2.00 |

The resulting composition is given in Table 5. The SPF, as measured by the in vivo method, is 9.0.

TABLE 5

| INGREDIENT | PERCENT |
| --- | --- |
| Hetester PHA | 10.00 |
| Finsolv TN | 10.00 |
| SAT-UFTR TiO$_2$ | 7.00 |
| Deionized Water | 61.65 |
| Veegum R | 0.70 |
| Keltrol F | 0.30 |
| Methylparaben | 0.15 |
| Deionized Water | 8.00 |
| Water-ethanol Oat Extract | 2.00 |
| Germall 115 | 0.20 |

EXAMPLE 2

The procedure of Example 1 is followed except that SAT-UFTR TiO$_2$ is not included in master batch (1) and the amount of deionized water in master batch (2) is increased by 7%.

EXAMPLE 3

A control example is prepared by the procedure of Example 1 except that the water ethanol oat extract is not included in master batch (4) and the amount of deionized water in batch (2) is increased by 2%. The SPF of the composition, as measured by the in vivo method, is 5.0.

EXAMPLE 4

Following the procedure of Example 1, a composition including ethyl ferulate in combination with the water ethanol oat extract is prepared by including 3% ethyl ferulate in master batch (1) and reducing the amount of deionized water in master batch (2) by three percent.

EXAMPLE 5

Following the procedure of Example 2, a composition including ethyl ferulate is provided by including 4% ethyl ferulate in master batch (1) and reducing the amount of deionized water in master batch (2) by 4%.

As mentioned, the sunscreen compositions of the invention conveniently may be employed in cosmetic preparations. Examples of cosmetic preparations are provided below, where weight percents are based on the total weight of the composition.

EXAMPLE 6

A cosmetic preparation in the form of a lipstick which employs the sunscreens of the invention is provided. The lipstick is produced by combining the compositions of Phase 1 and Phase 2 given below where weight percents are based on the total weight of the composition:

| | Weight Percent |
| --- | --- |
| Phase 1 | |
| D&C Red No. 7[1] | 3.0 |
| Castor Oil[2] | 10.0 |
| Phase 2 | |
| Candelilla Wax[3] | 12.0 |
| Carnauba Wax[3] | 10.0 |
| Beeswax[3] | 10.0 |
| Lantrol 1674[4] | 20.7 |
| Crodamol BS[5] | 14.0 |
| Castor Oil[2] | 10.0 |
| Propylparaben[6] | 0.3 |
| Ethanol Oat Extract | 5.0 |
| Ethyl Ferulate[7] | 5.0 |

[1]Warner-Jenkinson Co.
[2]CasChem
[3]Frank B. Ross
[4]Henkel Corp.
[5]Croda Surfactants Ltd
[6]Nipa Chemical Co., Japan
[7]Aldrich Chemical Co.

Phase 1 ingredients are ground on a Ross three roller mill until smooth. The resulting material is combined with phase 2 ingredients using a Lightnin™ stirrer, heated to 80° C., poured into a mold, and cooled to room temperature.

EXAMPLE 7

A cosmetic formulation in the form of a eye treatment gel employing the sunscreens of the invention is provided. The eye treatment gel is produced by combining Phases 1,2, and 3 given below:

|  | Weight Percent |
| --- | --- |
| Phase 1 | |
| Carbopol 940[1] | 1.25 |
| Deionized water | 61.95 |
| Methylparaben[2] | 0.30 |
| Triethanolamine[4] | 1.00 |
| Phase 2 | 30.00 |
| Lubragel MS[3] | |
| Phase 3 | |
| Aqueous oat extract | 0.50 |
| Deionized water | 5.00 |

[1]B. F. Goodrich
[2]Nipa Chemical Co., Japan
[3]Guardian Chemical Co.
[4]BASF Co.

Phase 1 is prepared by combining the components thereof with a Lightnin™ mixer, and heating to 70° C. The resulting mixture is cooled to 50° C., at which time Phase 2 is added and the resulting composition is mixed with a Lightnin™ mixer. This composition is further cooled to 30° C. at which time Phase 3 is added, and the resulting mixture is mixed with the Lightnin™ mixer and cooled to room temperature.

EXAMPLE 8

A cosmetic formulation in the form of a sun protection cream that employs the sunscreens of the invention is provided. The sun protection cream is produced by combining Phases 1,2, and 3 given below:

|  | Weight Percent |
| --- | --- |
| Phase 1 | |
| Arlacel 165[1] | 5.0 |
| Parsol MCX[2] | 5.0 |
| Robane[3] | 16.25 |
| Propylparaben[4] | 0.15 |
| Phase 2 | |
| Deionized Water | 51.05 |
| Tween 20[1] | 0.50 |
| Veegum Regular[5] | 1.75 |
| Methylparaben[4] | 0.30 |
| Phase 3 | |
| Water Ethanol Oat Extract | 5.0 |
| Deionized water | 15.0 |

[1]ICI Americas Inc.
[2]Givaudan Corp.
[3]Robeco Chemicals Inc.
[4]Nipa Chemical Co., Japan
[5]R. T. Vanderbilt Co., Inc.

Phase 1 ingredients are combined with a Lightnin™ mixer while heated to 78° C. Phase 2 ingredients are combined with a Lightnin™ mixer while heated to 75° C. Phases 1 and 2 are combined with a Lightnin™ mixer, and cooled to 30° C. to provide a blend. Phase 3 then is combined with the blend with the Lightnin™ mixer.

EXAMPLE 9

A cosmetic formulation in the form of a moisturizing cream that employs the sunscreens of the invention is provided. The moisturizing cream is produced by combining the compositions of Phases 1–3 given below:

|  | Weight Percent |
| --- | --- |
| Phase 1 | |
| Promulgen D[1] | 3.00 |
| Petrolatum[2] | 5.00 |
| Stearic Acid[3] | 4.00 |
| Trivent OC-16[4] | 23.00 |
| Propylparaben[5] | 0.15 |
| Phase 2 | |
| Deionized Water | 53.40 |
| Carbopol 934[6] | 0.40 |
| Methylparaben[5] | 0.30 |
| Triethanolamine[7] | 0.75 |
| Phase 3 | |
| Water Ethanol Oat Extract | 1.50 |
| Deionized Water | 8.50 |

[1]Amerchol Corp.
[2]Penreco
[3]Henkel Corp.
[4]Trivent Chemical Company Inc.
[5]Nipa Chemical Co. Japan
[6]B. F. Goodrich Co.
[7]BASF Corp.

Phase 1 ingredients are combined with a Lightnin™ mixer while heated to 72° C. Phase 2 ingredients are combined with a Lightnin™ in mixer while heated to 72° C. Phases 1 and 2 are combined with a Lightnin™ mixer and cooled to 30° C. to provide a blend. Phase 3 then is added to the blend and further mixed with a Lightnin™ mixer and cooled to room temperature to produce the sun protection cream.

Other useful cosmetic compositions which may be prepared and which incorporate the sunscreen agents of this invention include skin cleansers, tonics, moisturizers, sun care preparations, shampoos, hair conditioners, hair sprays, lip treatment preparations, color cosmetics, eye area treatment preparations, mascaras and nail treatment preparations.

While the present invention has been set forth in terms of specific embodiments thereof, it will be understood that numerous variations are now enabled to those skilled in the art. Accordingly, the invention is to be broadly construed and limited only by the scope of the appended claims.

What is claimed:

1. A sunscreen composition comprising an oat extract, a sunscreening agent, and a vehicle for enabling said composition to be applied to the skin.

2. The sunscreen composition of claim 1 wherein said vehicle is at least one of either water, gases, water-based liquids, oils, gels, emulsions, dispersions, or mixtures thereof.

3. The sunscreen composition of claim 1 wherein said vehicle is water, glycols, alcohols, or mixtures thereof.

4. The sunscreen composition of claim 1 wherein said vehicle is any one of either myristic acid, stearic acid, cetyl alcohol, stearyl alcohol, isopropyl myristate, diisopropyl adipate, caprylic/capric triglyceride, isododecane, petrolatum, beeswax, cyclomethicone, dimethicone, and dimethicone copolyol.

5. The sunscreen composition of claim 1 wherein said vehicle is any one of either water, ethanol, methanol, propanol, propylene glycol, butylene glycol, glycerine, polyoxyethylene (7) glyceryl triacetate, polyethylene glycol 200.

6. The sunscreen composition of claim 1 wherein said vehicle is any one of either trichlorofluoromethane, isopropanol, $C_{10}$-$C_{16}$ isoparaffins, and $C_{12}$-$C_{14}$ isoparaffins.

7. The sunscreen composition of claim 1 wherein said oat extract is obtained by treating an oat plant with an extraction agent selected from the group consisting of myristic acid, stearic acid, cetyl alcohol, stearyl alcohol, isopropyl myristate, diisopropyl adipate, caprylic/capric triglyceride, isododecane, petrolatum, beeswax, cyclomethicone, or dimethicone copolyol.

8. The sunscreen composition of claim 1 wherein said oat extract is obtained by treating an oat plant with an extraction agent selected from the group consisting of water, ethanol, a mixture of water and ethanol, methanol, propanol, propylene glycol, butylene glycol, glycerine, polyoxyethylene (7), glyceryl triacetate, or polyethylene glycol 200.

9. The sunscreen composition of claim 1 wherein said oat extract is extracted from a mixture obtained by treating an oat plant with an extraction agent selected from the group consisting of trichlorofluoromethane, isopropanol, $C_{10}$-$C_{16}$ isoparaffins, or $C_{12}$-$C_{14}$ isoparaffins.

10. The sunscreen composition of claim 5 wherein said oat extract is obtained by treating an oat plant with an extraction agent selected from the group consisting of water, ethanol or a mixture of water and ethanol.

11. The sunscreen composition of claim 1 further including a dihydroxycinnamic acid derivative.

12. The sunscreen composition of claim 2 wherein said sunscreen agent is titanium dioxide.

13. The sunscreen composition of claim 11 wherein the derivative is ferulic acid.

14. The sunscreen composition of claim 11 wherein the derivative is ethyl ferulate.

15. The sunscreen composition of claim 1, wherein said oat extract is obtained by treating an oat plant with an extraction agent of either one or more alcohol mixtures, glycols, oil, hydrocarbons, silicones, fatty acid derivatives, waxes, or mixtures thereof.

16. The sunscreen composition of claim 1, wherein the oat extract is present in an amount of about 0.1 to 50% by weight.

17. The sunscreen composition of claim 1, wherein the oat extract is present in an amount of about 0.5 to 15% by weight.

18. The sunscreen composition of claim 11 wherein the dihydroxycinnamic acid derivative is present in an amount of about 0.05 to 25% by weight.

19. The sunscreen composition of claim 11 wherein the dihydroxycinnamic acid derivative is present in an amount of about 0.5 to 10%.

20. A sunscreen composition comprising an oat extract, a sunscreening agent, and a vehicle for enabling the composition to be applied to the skin, wherein the oat extract is obtained by: washing ground oat plant material in a solution of chloroform and methanol, separating the plant material from the solution, drying the separated plant material, treating the dried plant material with an extraction agent to form a mixture, removing undissolved plant material from the mixture, concentrating and drying the mixture to provide a residue of the plant extract, washing the reside with an ethanol solution, filtering and drying the plant extract.

21. The sunscreen composition of claim 20, wherein the extraction agent comprises a mixture of water and ethanol.

* * * * *